United States Patent
Kojima et al.

(10) Patent No.: US 9,482,629 B2
(45) Date of Patent: Nov. 1, 2016

(54) X-RAY CT APPARATUS

(75) Inventors: Shinichi Kojima, Hitachinaka (JP);
Fumito Watanabe, Kashiwa (JP);
Hironori Ueki, late of, Hachioji (JP);
Yasutaka Konno, Saitama (JP); Yushi Tsubota, Hitachi (JP); Yukiko Ueki, legal representative, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 432 days.

(21) Appl. No.: 13/701,232

(22) PCT Filed: Jun. 3, 2011

(86) PCT No.: PCT/JP2011/062794
§ 371 (c)(1),
(2), (4) Date: Jan. 7, 2013

(87) PCT Pub. No.: WO2011/152517
PCT Pub. Date: Dec. 8, 2011

(65) Prior Publication Data
US 2013/0108009 A1    May 2, 2013

(30) Foreign Application Priority Data
Jun. 3, 2010    (JP) .................. 2010-127401

(51) Int. Cl.
*G01N 23/083*  (2006.01)
*G01N 23/04*   (2006.01)
*A61B 6/03*    (2006.01)
*A61B 6/00*    (2006.01)

(52) U.S. Cl.
CPC ............. *G01N 23/046* (2013.01); *A61B 6/032* (2013.01); *A61B 6/5258* (2013.01); *A61B 6/585* (2013.01); *A61B 6/5205* (2013.01); *A61B 6/5282* (2013.01); *A61B 6/583* (2013.01)

(58) Field of Classification Search
CPC ...... G01N 23/046; A61B 6/03; A61B 6/032; A61B 6/5205; A61B 6/5258; A61B 6/5282; A61B 6/583; A61B 6/585
See application file for complete search history.

(56) References Cited

U.S. PATENT DOCUMENTS

| 2006/0289765 A1 | 12/2006 | Ikhlef et al. |
| 2012/0166128 A1* | 6/2012 | Ikhlef .................. A61B 6/583 |
| | | 702/104 |

FOREIGN PATENT DOCUMENTS

| JP | 11-253432 A | 9/1999 |
| JP | 2005-253815 A | 9/2005 |
| JP | 2008-142146 A | 6/2008 |

OTHER PUBLICATIONS

Chinese Office Action received in Chinese Application No. 201180027204.9 dated Jul. 28, 2014.

* cited by examiner

*Primary Examiner* — Robert Kim
*Assistant Examiner* — Eliza Osenbaugh-Stewar
(74) *Attorney, Agent, or Firm* — Mattingly & Malur, PC

(57) ABSTRACT

An X-ray CT apparatus includes: an X-ray generating unit configured to generate an X ray; an X-ray detecting unit including a plurality of X-ray detectors, each configured to detect the X ray generated from the X-ray generating unit and transmitted through an object; and an image generating unit configured to correct and reconstruct signals acquired by the X-ray detecting unit. While crosstalk correction of a plurality of the X-ray detectors is performed at the image generating unit, correction of a locally attenuating component is previously performed and correction of a whole component of the crosstalk is performed when the image is reconstructed.

9 Claims, 8 Drawing Sheets

(a)

(b)

Signal quantity when light is applied to only 321a (c)

Signal quantity when light is applied to only 321b (a)

(b)

Signal quantity when light is applied to only 321c (c)

Signal quantity when light is applied to only 321d (a)

(b)

X-RAY CT APPARATUS

TECHNICAL FIELD

The present invention relates to an X-ray CT (computed tomography) apparatus with correction of crosstalk in an X-ray detector.

BACKGROUND ART

Description of the Related Art

An X-ray CT apparatus is a device, including an X-ray source for emitting an X ray toward an object, an X-ray detector for detecting the X ray transmitted through the object at a position opposite to the X-ray source to scan an image, for reconstructing an image with a data processing system from a difference in X-ray absorbing ratio inside the object on the basis of data of projection in a plurality of directions obtained by scanning the object with rotation motion using the data processing system.

The X ray incident to the detector is converted into photons (fluorescence). The photon is photoelectrically converted with a photodiode in the detector into an electric signal to be processed in a circuit at a rear stage.

However, a part of the signal is converted into an electric signal by detectors other than the detector to which the signal is incident. This phenomenon is called crosstalk.

There are kinds of crosstalk, i.e., X-ray crosstalk in which an X ray scattered inside the detector is detected by another detector, and photo-crosstalk, i.e., the photon converted from the X ray is photo-converted with a photodiode after movement of the photon to adjacent detector. When the crosstalk occurs, an image may become blurred or an artifact may occur.

Patent Document 1 discloses a technology in which a quantity of crosstalk is previously estimated for correction. Patent Document 2 discloses a technology in which a speed of calculating crosstalk correction and reconstructing the image is increased.

PRIOR ART DOCUMENT

Patent Document

[Patent Document 1] JP2005-253815 A
[Patent Document 2] JP 2008-142146 A

SUMMARY OF INVENTION

Problems to be Resolved by Invention

However, in the technology disclosed in Patent document 1 in which a quantity of crosstalk is previously estimated for correction, because there is a problem in decrease in response due to calculation, the technology is not necessarily sufficient when this technology is used in an X-ray CT apparatus to grasp a status of an emergency patient, In addition, in the method of increasing the calculation speed disclosed in Patent document 2, there is a problem in calculation cost for this process (addition of parts for forming the calculator and use of a high performance part).

The present invention aims to decrease in calculation quantity during crosstalk correction in an X-ray CT apparatus and to enhance a calculation throughput.

Means for Resolving the Problems

To overcome the above-described problem, the present invention provides a configuration below to achieve the object.

That is, in an X-ray CT apparatus, comprising:
an X-ray generating unit configured to generate an X ray;
an X-ray detecting unit including a plurality of X-ray detectors, each configured to detect the X ray generated from the X-ray generating unit and transmitted through an object; and
an image generating unit configured to correct a signal acquired by the X-ray detecting unit and reconstruct an image,
wherein while crosstalk correction of a plurality of the X-ray detectors is performed at the image generating unit, correction of a locally attenuating component is previously performed and correction of a whole component of crosstalk is performed when the image is reconstructed.

Advantageous Effect

According to the present invention, a calculation quantity during the crosstalk correction will decrease, so that a calculation through put is enhanced.

EMBODIMENTS OF INVENTION

First to third embodiments will be described.

First Embodiment

With reference FIGS. 1 to 4, will be described a first embodiment.

First, "outline configurations of an X-ray CT apparatus", and configurations of "an X-ray tube, an X-ray detector, an imaging unit, and imaging means", "an image generating unit", etc. will be described.

After that, will be described "a flow chart for acquiring crosstalk correction data", as well as "Measuring a signal spreading from each detector", "Correcting sensitivity correction", "Calculating a whole component for correction", and "calculating locally attenuating components" in the flowchart. In addition, in "the flow of scanning", will be described "scanning condition setting step", and "scanning step". In addition, "imaging", to be originally included in the "flow of scanning", will be described as "imaging data". Next, will be described the methods above.

After that, will be explained that this method accords with a theoretical bases by "demonstration in validity in that in the crosstalk correction, locally attenuating components and whole components can be separately corrected".

In addition, will be explained "expected advantageous effect" of this method.

The subjects above will be described subsequently.

<Outline Configuration of X-Ray CT Apparatus>

Will be described an X-ray CT apparatus 100 to which the present invention is applied.

Figure 1:
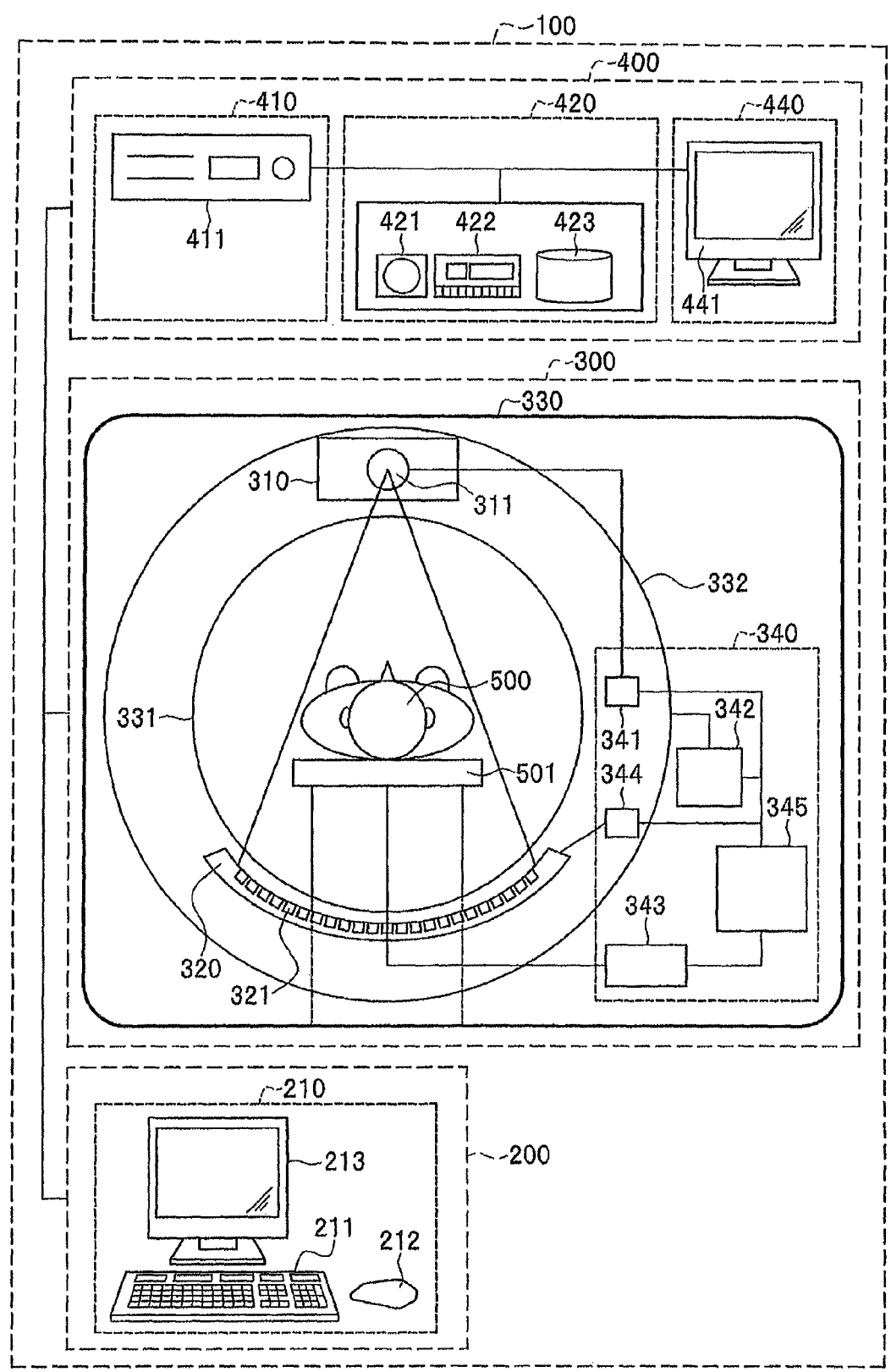
FIG. 1 is a configuration drawing to show an outline of an X-ray CT apparatus in embodiments of the present invention.

FIG. 1 is a configuration drawing to show an outline of an X-ray CT apparatus in embodiments of the present invention.

In FIG. 1, the X-ray CT apparatus 100 includes an input unit 200, a scanning unit 300, and an image generating unit 400.

The scanning unit 300 includes an X-ray generating unit 310, an X-ray detecting unit 320, a gantry 330, a scanning control unit 340, and an object mounting table 501.

The image generating unit 400 includes a signal collecting unit 410, a data processing unit 420, and an image display unit 440.

A scanning condition input unit 210 in the input unit 200 includes a keyboard 211, a mouse 212, and a monitor 213. The monitor 213 may have a touch panel function to be used as an input unit.

It is not necessarily required that the input unit 200 and the image generating unit 400 are integral with the X-ray CT apparatus 100. For example, the operation can be provided with another unit connected thereto through a network.

In addition, it is possible to provide a unit having both functions of the image generating unit 400 and the input unit 200.

The X-ray generating unit 310 in the scanning unit 300 includes an X-ray tube 311. In addition, the X-ray detecting unit 320 includes an X-ray detector 321.

At a middle of the gantry 330, there are provided an opening 331 having a circular shape for disposing the object mounting table 501. Within the gantry 330, a rotating plate 332 for mounting the X-ray tube 311 and the X-ray detector 321, and a drive mechanism (not shown) for rotating the rotating plate 332 are provided.

The object mounting table 501 has a drive mechanism (not shown) for adjusting a position of the object body 500 relative to the gantry 330.

The scanning control unit 340 includes: an X-ray control unit 341 for controlling the X-ray tube 311, a gantry control unit 342 for controlling a rotating drive for the rotating plate 332, a table control unit 343 configured to control driving the object mounting table 501, a detector control unit 344 for controlling scanning in the X-ray detector 321, and a supervisory control unit 345 for controlling a flow of operations of: the X-ray control unit 341, the gantry control unit 342, the table control unit 343, and the detector control unit 344.

<X-Ray Tube, X-Ray Detector, and Scanning Unit>

In this embodiment, a distance between an X-ray generating point of the X-ray tube 311 and an X-ray input plane of the X-ray detector 321 is set to 1000 mm. A diameter of the opening 331 of the gantry 330 is set to 700 mm in this embodiment.

The X-ray detector 321 comprises a known X-ray detector comprising a Scintillator (emitting florescent light in response to an X-ray and ionization radiation), or a photo-diode (converting light such as fluorescence into an electric signal). The X-ray detector 321 has such a configuration that a lot of detecting elements are arranged in an arc shape equidistantly from the X-ray generating point of the X-ray tube 311. The number of the elements (the number of channels) is, for example, 1000. A size of each detecting element in a channel direction is, for example, 1 mm.

Required time of rotating the rotating plate 332 depends on a parameter inputted with the scanning condition input unit 210 by a user. In this embodiment, the required time of rotating is defined to be 1.0 s/rotation.

The number of times of scanning by the scanning unit 300 per one rotation is 900, that is, scanning is once every rotation of 0.4 degree.

These specifications are not limited to these value and can be modified and changed depends on the configuration of the X-ray device.

<Image Generating Unit>

The image generating unit 400 includes the signal collecting unit 410, the data processing unit 420, and the image display unit 440.

The signal collecting unit 410 includes a data acquisition system (hereinafter referred to as DAS) 411. The DAS 411 converts a detection result of the X-ray detector 321 described above into a digital signal.

The data processing unit 420 includes a central processing unit (CPU) 421, a memory 422, and a HDD (Hared disk drive) device 423. Various processes such as correction calculation and reconstructing process of the image are conducted by loading and activating a predetermined program in the memory 422 by the central processing unit 421. The HDD device 423 performs inputting, holding, and outputting data.

Cathode Ray Tube

The image display unit 440 includes the image display monitor 441 such as a crystal display and a CRT (Cathode Ray Tube).

<Flowchart for Acquiring Crosstalk Correction Data>

With reference to the flowchart in FIG. 2 will be described a method and means of acquiring the crosstalk correction data by the X-ray CT apparatus 100 (see FIG. 1).

Figure 2:
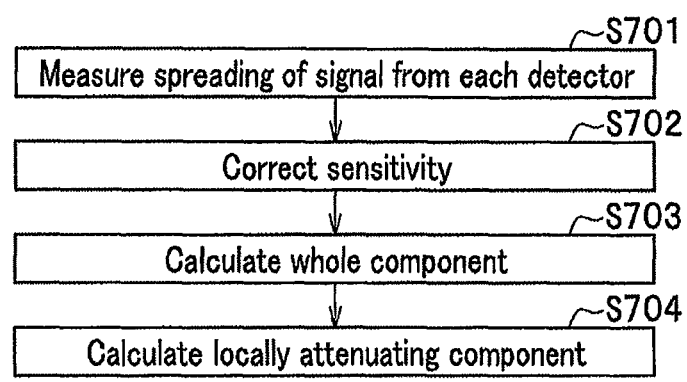
FIG. 2 is a flowchart showing a method of acquiring crosstalk correction data in a first embodiment of the present invention.

FIG. 2 is a flowchart showing the method of acquiring the crosstalk correction data in the first embodiment of the present invention. The flowchart includes "Measuring signal spreading from each detector", "Correcting sensitivity", "Calculating whole component", and "Calculating locally attenuating component".

[Measuring Signal Spreading from Each Detector]

First, the signal spreading from each detector (X-ray detectors) is measured (step S701).

Figure 3:
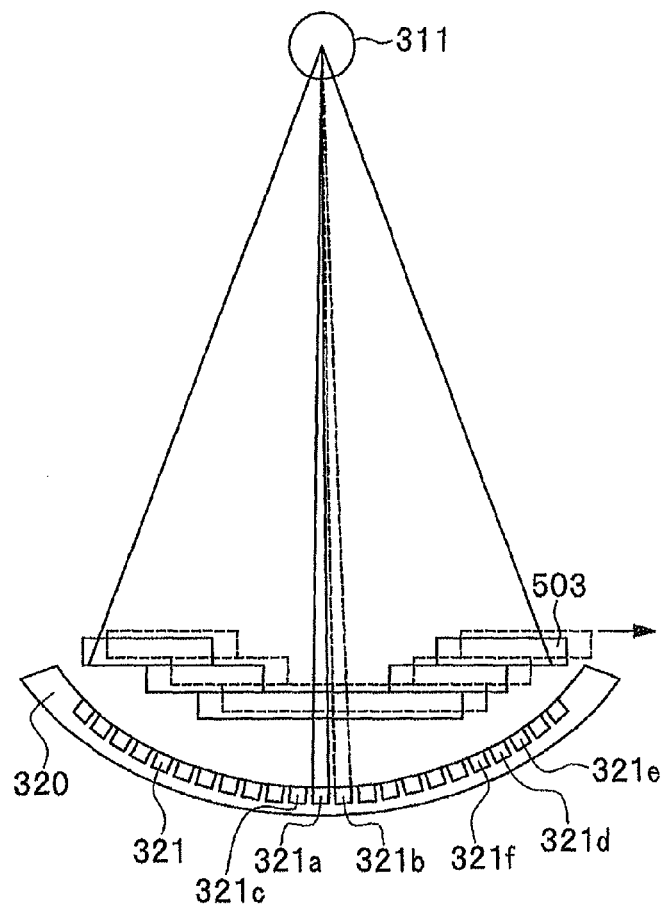
FIG. 3 is an illustration showing a method of measuring a crosstalk quantity in the first embodiment of the present invention, wherein (a) is an illustration showing measurement of a signal with an X-ray detector and a shielding body, (b) is a chart showing a distribution of signal quantity when light is applied to only an X-ray detector 321a, and (c) is a chart showing a distribution of a signal quantity when light is applied to only an X-ray detector 321b.
Figure 3:
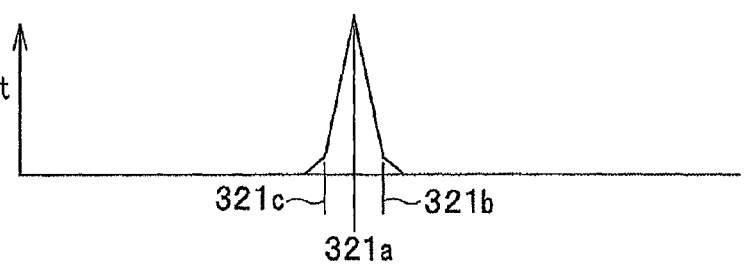
Figure 3:
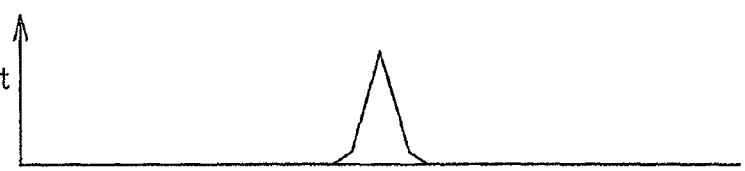

With reference to FIG. 3 will be described a measuring method.

FIG. 3 is an illustration showing a method of measuring a crosstalk quantity in the first embodiment of the present invention. As shown in FIG. 3(a), a signal is measured with a shielding body 503 designed to cause an X-ray signal and light generated from the X-ray signal to be incident to only one X-ray detector 321a.

In this operation, it is assumed in the embodiment that in addition to the X-ray detector 321a, an X-ray detector 321b and an X-ray detector 321c on both sides of the X-ray detector 321a measure signals of light secondarily emitted (the X ray is primary). FIG. 3 (b) shows a distribution of signal quantity when light is applied to only the X-ray detector 321a, and FIG. 3 (c) shows a distribution of a signal quantity when light is applied to only the X-ray detector 321b.

Next, the shielding body 503 is shifted to cause the X-ray signal and light generated from the X-ray signal to be incident to only the X-ray detector 321b and measurement is performed. This measurement provides measurement of the signal to be originally incident and signals of light secondary emitted therearound.

In this operation, quantities of incident light to the respective X-ray detectors are tried to be equalized. For example, when there is a distribution of light quantities of the X ray (signal quantities when light is respectively applied only to the X-ray detector 321a and the X-ray detector 321b in FIG. 3), the distribution of a light quantity of the X ray is previously measured, and the signal quantities are normalized to a signal quantity of a reference light quantity.

As a result, if leaked quantities due to crosstalk of all the X-ray detectors 321 are the same, the signal to be originally incident to the X-ray detector will have a value proportional to a sensitivity of the X-ray detector. Because a crosstalk quantity has almost no change when the X-ray detector having the same size is illuminated with the same light quantity, there is almost no error caused by assumption in that leaked quantities due to crosstalk of all the X-ray detectors 321 are the same. As a result, it becomes possible to calculate the sensitivity of each of the X-ray detectors 321 from the signal to be originally incident to the X-ray detector, so that sensitivity correction data can be prepared. More specifically, the data is an inverse number of a value to which a signal quantity of a reference light quantity when the signal is directly incident to each X-ray detector 321 is normalized.

[Sensitivity Correction]

Description of the flowchart in FIG. 2 will be continued.

Next, sensitivity correction is performed (step S702).

With data acquired in the step S701, the sensitivity correction is made also for the signal spreading quantities obtained in the step S701.

A method of sensitivity correcting will be described below.

Measuring data is divided by the signal, measured in the step S701, to be originally incident to the X-ray detector when the shielding body 503 is used to correct difference in the sensitivity among the respective detectors. For example, in a step S701, when a position of the shielding body 503 is set so that light is applied to only the X-ray detector 321a, signals are generated also in the X-ray detector 321b and the X-ray detector 321c on both sides of the X-ray detector 321a.

In this instance, the signal of the X-ray detector 321b is a signal caused by crosstalk, but includes a sensitivity error of each X-ray detector. Accordingly, when the detector to which a signal is to be originally incident is the X-ray detector 321a, the signal detected by the X-ray detector 321b is divided by a signal quantity generated when the X-ray detector to which a signal is to be originally incident is the X-ray detector 321b to provides a signal quantity normalized to the reference light quantity.

In addition, regarding the X-ray detector 321a, the signal detected by the X-ray detector 321a is divided by the signal generated when the X-ray detector to which the signal is originally incident is the X-ray detector 321a. Because this means that the value is divided by the same value, the value after correction of the signal of the X-ray detector to which the signal is originally incident becomes necessarily 1. The X-ray detector other than the X-ray detector to which the signal is originally incident indicates a signal quantity generated when light of 1 is applied to the X-ray detector to which signal is originally incident. The signal other than the signal of the X-ray detector to which light is to be originally incident is a crosstalk quantity.

[Calculating Whole Component]

A whole component of the crosstalk correction is calculated from data after the sensitivity correction acquired in the steps S701 and S702 (step S703).

An example of method of calculating the whole component is shown. At first, a total of the signal quantities other than the signal originally incident to each detector is acquired.

In this example, when the X-ray detector to which the signal is to be originally incident is the X-ray detector 321a, because signals are generated by the X-ray detector 321b and the X-ray detector 321c on both sides of the X-ray detector 321a, a sum of the two signals is calculated. In a channel of which the signal quantity becomes maximum, the channel is treated as a reference channel because there is no attenuation in the channel, and a crosstalk quantity in the channel is defined as a correction quantity for the whole component.

For example, in this example, when the X-ray detector in which the total of the signal quantities other than the signal of the X-ray detector to which the signal is originally incident is the X-ray detector 321a, the crosstalk quantity of the X-ray detector adjacent to and on the right hand of the X-ray detector 321a is a value of the X-ray detector 321b after the sensitivity correction is performed, and the crosstalk quantity of the X-ray detector adjacent to and on the left hand of the X-ray detector 321a is a value of the X-ray detector 321c after the sensitivity correction is performed.

In addition, if there are a plurality of channels showing maximum values, it can be allowed to average these values.

[Calculating Locally Attenuating Component]

At last, the locally attenuating component will de described (step S704).

A locally attenuating component of each channel is a difference between a correction quantity of each channel and the correction quantity of the whole component acquired in the step S703. The value is calculated for all channels.

In this example, the reference channel in the step S703 is the X-ray detector 321a. A calculation example of the locally attenuating component in the X-ray detector 321d in this status will be described.

Because the signal quantity incident to the X-ray detector 321d is normalized to 1, this is not a target of calculation. Regarding an X-ray detector 321e and an X-ray detector 321f on both sides of the X-ray detector 321d, a difference between the X-ray detector 321b and the X-ray detector 321c on both sides of the X-ray detector 321a which is the reference channel is calculated. For example, the locally attenuating component in the X-ray detector 321e is acquired by (the X-ray detector 321e)–(the X-ray detector 321b).

Similarly, the locally attenuating component in an X-ray detector 321f is acquired by (the X-ray detector 321f)–(the X-ray detector 321c). The values of these locally attenuating components may become negative.

In a case where the locally attenuating component is low, the correction quantity can be approximately set to zero. For example, a threshold (for example, 5%) is set, so that if the error is not larger than the threshold, the correction quantity can be set to 0, etc.

As described above, the correction quantity is determined as a local attenuation correction data. This is used in reconstructing the image described later.

<Flow of Scanning Image>

Next, a flow of scanning an image with the X-ray CT apparatus 100 will be shown. Scanning image includes three steps, that is, "Scanning condition setting", "Scanning Image", and "Imaging". However, "Imaging" will be described with a flowchart at a different item as "data imaging".

[Scanning Condition Setting Step]

A scanning condition setting step will be described. The scanning condition input unit 210 in FIG. 1 displays an input screen image on the monitor 213 or another monitor. An operator operates the mouse 212, the keyboard 211, or a touch panel sensor equipped in the monitor 213 forming the scanning condition input unit 210 while watching the screen image, in order to provide setting of a tube current, a tube voltage, of the X-ray tube 311, and an imaging region of the object body 500, etc. In addition, when the scanning condition has been previously stored, it is also possible to read out and use the scanning condition. In this case, the operator is not required to enter the condition at every time of scanning.

[Scanning Step]

Next, the scanning step will be described. In the scanning step, when the operator commands start of scanning, scanning and imaging are performed under the conditions of the scanning range, the tube voltage, and tube current quantity which have been set in the scanning condition input unit 210 by the operator in the scanning condition setting step.

An example of a specific method will be described. At first, the object body 500 is placed on the object mounting table 501.

The supervisory control unit 345 in FIG. 1 commands the table control unit 343 to move the object mounting table 501 in a direction vertical to the rotating plate 332 and stops movement when a scanning position of the rotating plate 332 agrees with the specified scanning position. This completes arrangement of the object body 500.

The supervisory control unit 345 transmits a command to start rotation of the rotating plate 332 by causing the gantry control unit 342 to operate a drive motor at the same timing.

When rotation of the rotating plate 332 becomes in a constant speed status and arrangement of the object body 500 is completed, the supervisory control unit 345 commands X-ray illuminating timing for the X-ray tube 311 to the X-ray control unit 341 and scanning timing of the X-ray detector 321 to the detector control unit 344. Then, the scanning is started. A whole of the imaging region is scanned by repeating these commands.

In addition, movement and stop of the object mounting table 501 is repeated. However, as known as Helical Scan, scanning can be provided while the 501 is moved.

An output signal of the X-ray detector 321 is converted into a digital signal by the DAS 411 equipped in the signal collecting unit 410 and then, once stored in the HDD device 423 for convenience of process of imaging described later.

<Imaging from Data>

Figure 4:
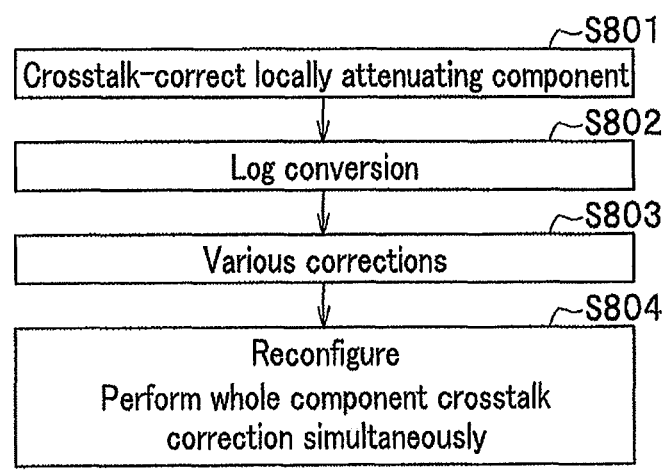
FIG. 4 is a flowchart showing a process of imaging with data stored with crosstalk correction in the first embodiment of the present invention.

Next, with reference to FIG. 4 will described steps of imaging from the stored data.

FIG. 4 is a flowchart showing a process of imaging from data stored with crosstalk correction in the first embodiment of the present invention.

In FIG. 4, all calculation in the steps of imaging is performed with the central processing unit 421, the memory 422, and the HDD device 423 equipped in the data processing unit 420 shown in FIG. 1.

First, "Crosstalk-correct local attenuating component", which is local attenuation correction, is performed (step S801).

The local attenuation correction data made in "Calculate local attenuating component" in the step S704 is used as corrected values.

After that, "Log Conversion (log conversion) is performed (S802).

The reason for performing the Log conversion is as follows:

Generally, signals of an X ray and light attenuate exponentially in transmission and scattering of the X-ray signal and the light signal. Accordingly, once the signal is Log-converted in a calculating process, it is known that this is convenient for calculating because it is generally frequent that a calculating amount of product is reduced to a calculation amount of summing.

Next, "Various corrections" which are other corrections is performed (step S803).

This correction is performed in step S803 when there is an item or phenomenon to be corrected in addition to the local attenuation correction, i.e., "Crosstalk-correct local attenuating component" (step S801) Accordingly, there may be a case where the "Various correction" in step S803 is not performed.

After that, "Reconfigure, Perform whole component crosstalk correction simultaneously", where reconfiguration is performed while correction to the whole with the correction data of the whole component prepared in the step S703 in FIG. 2 is performed at the same time.

Here, "at the same time" is not strict meaning of "at the same time", but rather meaning of "as well as".

At last, the image after reconstruction, obtained in the step S804, is stored in the HDD device 423 (see FIG. 1). The stored image is displayed on the image display monitor 441 (FIG. 1) in response to a command by a user or automatically. The user makes a diagnosis with the image.

As mentioned above, "Crosstalk correction for locally attenuating component", being a local attenuation correction, is performed in the step S801, and "Reconfigure, Perform whole component crosstalk correction simultaneously" is performed in the step S804. As described above, that the crosstalk correction is divided is a feature of the embodiment.

Next, it will be demonstrated that there is approximately no problem in dividing the crosstalk correction into the step S801 and the step S804 with explanation.

<Demonstration Regarding Justification in Capability of Dividing Correction into Locally Attenuating Component Correction and Whole Component Correction in Crosstalk Correction>

In FIG. 3, a signal incident to the X-ray detector 321a at a position x in a plurality of the X-ray detectors 321 arranged in the X-ray detecting unit 320 is defined as m(x). In addition, the signal detected by the X-ray detector 321a is defined as S(x). The incident signal m(x) is generally not equal to the detection signal S(x) because the signal is scattered or receives noise from others and expressed by Eq. (1).

[Eq. (1)]

$$S(x) = m(x) + \sum_t m(t)g(x-t) - \sum_t d_{tx} m(t) \quad (1)$$

Here, "t" represents a discrete position (not time). A term g(x-t) is a spread function of blur of crosstalk, "$d_{tx}$" represents a local signal attenuation coefficient from an X-ray detector t to an X-ray detector x.

Assuming that the signal in which the locally attenuating component is corrected is defined as S'(x), Eq. 2 is given:

[Eq. (2)]

$$S'(x) = m(x) + \sum_t m(t)g(x-t) \equiv m(x) + P(x) \quad (2)$$

When S'(x) is logarithmic-converted (log-converted) with assumption of S(x)>>P(x) and m(x)>>P(x), Eq. (3) is given from Eq. (2).

[Eq. (3)]

$$\log(S'(x)) = \log\{m(x) + P(x)\} \quad (3)$$
$$= \log\left\{m(x)\left(1 + \frac{P(x)}{m(x)}\right)\right\}$$
$$= \log(m(x)) + \log\left(1 + \frac{P(x)}{m(x)}\right)$$

Here, because due to m(x)>>P(x), (P(x)/m(x)) is sufficiently smaller than 1, Eq. (3) can be modified into Eq. (4) using (log(1+x)≈x), which is a first-order Taylor expansion approximation of log(1+x). In addition, here (P(x)/m(x)) is assumed to be x in (log(1+x))≈x) described above.

[Eq. (4)]

$$\log(S'(x)) \approx \log(m(x)) + \frac{P(x)}{m(x)} = \log(m(x)) + \frac{\sum_t m(t)g(x-t)}{m(x)} \quad (4)$$

Our attention is directed to that Σg(t)=0 can be established, because the signal of which the attenuating component is corrected is used. This means that the signal leaked from one X-ray detector is all detected by other X-ray detectors. In that case, correction is possible with an image filter.

For example, the spread function is considered with assumption that the signal spreads to only the X-ray detectors on both sides.

[Eq. (5)]

$$g(x-t) = -2w(t=x) \quad (5)$$
$$= w(t = x \pm 1)$$
$$= 0 \text{ Others}$$

This Eq. (5) has an assumption that a signal is subject to influence from and gives influence to the X-ray detectors on both sides, i.e., left and right sides. This means that the X-ray detector is subject to "w" of crosstalk signals from the left and right X-ray detectors (t=x±1) respectively, and "2w" of the crosstalk signal scatters and leaks from the X-ray detector itself (-2w). Here, "w" is a constant representing a signal intensity of crosstalk. In addition, in (Eq. 5), Σg(t)=0 is established.

Here, if it is assumed that variation in the signal quantity is gradual, Eq. (4) can be further modified into Eq. (6).

[Eq. (6)]

$$\log(S'(x)) = \log(m(x)) + \frac{w(m(x-1) + m(x+1)) - 2wm(x)}{m(x)} \quad (6)$$
$$= \log(m(x)) + w\frac{m(x-1)}{m(x)} + w\frac{m(x+1)}{m(x)} - 2w$$
$$= \log(m(x)) + w\left(\frac{m(x-1)}{m(x)} - 1\right) + w\left(\frac{m(x+1)}{m(x)} - 1\right)$$

Here, if it is assumed that a signal variation of "m(x)" is gradual, because m(x-1) and m(x) are adjoined each other and values are close to each other, (m(x-1)/m(x))≈1. Accordingly m(x-1)/m(x)-1≈0. In other words, if it is assumed that (m(x-1)/m(x)-1) is considered as x in the first-order Taylor expansion approximation of log(1+x), that is, (log(1+x)≈x), the following equation modification will become possible. In addition, because m(x+1) and m(x) are adjoined each other, and values are close to each other, the following equation modification is possible because of the reason used in the relation between m(x-1) and m(x).

Accordingly Eq. (6) can be approximated by Eq. (7) below.

[Eq. (7)]

$$\log(m(x)) + w\left(\frac{m(x-1)}{m(x)} - 1\right) + w\left(\frac{m(x+1)}{m(x)} - 1\right) \approx \quad (7)$$
$$\log(m(x)) + w\log\left(1 + \frac{m(x-1)}{m(x)} - 1\right) + w\log\left(1 + \frac{m(x+1)}{m(x)} - 1\right) =$$
$$(1 - 2w)\log(m(x)) + w\log(m(x-1)) + w\log(m(x+1))$$

In addition, the above described approximation is used in the first to second equation modification in Eq. (7).

Accordingly, Eq. (8) is given:

[Eq. (8)]

$$\log(S'(x)) \approx (1-2w)\log(m(x)) + w\log(m(x-1)) + w\log(m(x+1)) \quad (8)$$

It was assumed in the above description that the influence spreads to only the adjoining X-ray detectors. However, generally, only when Σg(t)=0, Eq. (8) can be expressed in Eq. (9) using a similar approximation.

[Eq. (9)]

$$\log(S'(x)) = \sum_i a_i \log(m(x+i)) \quad (9)$$

In Eq. (9), S'(x) is detected by the X-ray detector and becomes a known value when correction is performed. If m(x) can be calculated from this known S'(x), the X-ray signal incident to the X-ray detector 321 in which the influence of crosstalk is removed can be known. In other words, X-ray signal m(x) that will result in construction of a true image can be known.

When log(S(x)) is expressed as a close approximation of Eq. (9) with a sum of products of log(m(x)) and its coefficient, a method of acquiring log(m(x)) from log(S(x)) is possible using a known deconvolution method. The difference in equations is S'(x) and S(x). Accordingly, because Eq. (9) has been acquired, conversion from log(S'(x)) to log(m (x)) is possible by the known deconvolution method.

As described above in this embodiment, the known deconvolution method can be used. In addition, in the conventional known example, the deconvolution method is applied to S(x), whereas in this embodiment, it is applied to S'(x). Because S'(x) is a signal which have been subject to correction, m(x) which will result in structuring an image at an accuracy higher than that in case where the conventional S(x) is used can be restructured.

In Eq. (9), if it is assumed that a relational expression of log(S'(x)), log(m(x)), and their coefficient "$a_i$" is expressed as a determinant, an inverse determinant of the coefficient "$a_i$" will be necessary in a process of calculating log(m(x)). The inverse determinant of the coefficient "$a_i$" is directly calculated from Eq. (9), and is used as a deconvolution filter in calculation on software, which provides correction to the whole. The calculations are possible even after the Log conversion.

As described above, it can be understood that the method of correction and reconstruction based on the procedure in the flowchart in FIG. 4 is approximately established. Using this result, deconvolution is performed on the reconstruction filter, which provides the cross talk correction.

In FIG. 4, "Crosstalk-correct local attenuating component" in the step S801 is conversion from S(x) to S'(x) by Eq. (1) and (2). Because the conversion from S(x) to S'(x) is before the Log conversion in the next step S802, this assures $\Sigma g(t)=0$.

In addition, the "Log conversion" in the step S802 corresponds to the conversion from Eq. (2) to Eq. (3).

The "Various corrections" in step S803 is other than the correction described above, and there is no correspondence in from Eq. (1) to Eq. (9).

If there is a necessary correction, additional correction is performed before the reconstruction of the image to reflect it in reconstruction of the whole image.

In addition, "Reconstruct and perform whole component crosstalk correction simultaneously" in the step S804 corresponds to a step of performing correction and reconstruction of the image by using Eq. (9) and calculation of deconvolution described above.

Expected Advantageous Effect

In this embodiment, there are advantageous effects below.

[1] Once the deconvolution filter is obtained, the crosstalk correction of the whole component takes not so long time the crosstalk correction of the whole component, and the locally attenuating component is corrected by only a quantity in which a trend of the whole is removed, so that a calculation quantity becomes largely reduced. Accordingly, the calculation time period can be shortened.

[2] In this embodiment, the locally attenuating components are previously corrected, which is proper in accuracy in linear approximation. If the crosstalk correction is performed after the Log conversion, correction cannot be expressed by a simple deconvolution filter because $\Sigma g(t)=0$ is not assured. As a result, an error will be generated, which may be a cause of an artifact. The method of the present invention has an accuracy which is higher than that with the simple deconvolution after the Log conversion.

In this embodiment, though the sensitivity is measured at the same time with the shielding body 503, the sensitivity can be measured by another method. In addition, the method of acquiring the locally attenuating components and the whole component is only an example, and it can be acquired by another method.

Second Embodiment

In the first embodiment, the example in which the local attenuation depends on every X-ray detector is shown. However, the second embodiment shows a case where attenuation of crosstalk is generated with a predetermined pattern in accordance with a configuration of the X-ray detectors.

For example, if the X-ray detecting unit is configured with a module including a plurality of X-ray detectors connected, local influence of crosstalk may vary at connection between modules. At an edge of the module, there may be cases where a size between detectors becomes large and there is a gap for facilitating manufacturing. On the other hand, because the X-ray detectors near the middle of the module are equidistantly arranged, characteristics of the X-ray detectors near the middle of the module are close to each other. As a result, it is frequent that the crosstalk quantity varies only at the edge part of the module. In this case, a method of acquiring correction values can be simplified.

The method of acquiring the correction value will be described in such a case.

<Simplified Method of Acquiring Correction Value>

The X-ray detecting unit and related members and configuration and a method of measuring a crosstalk quantity in the second embodiment will be described.

Figure 5:
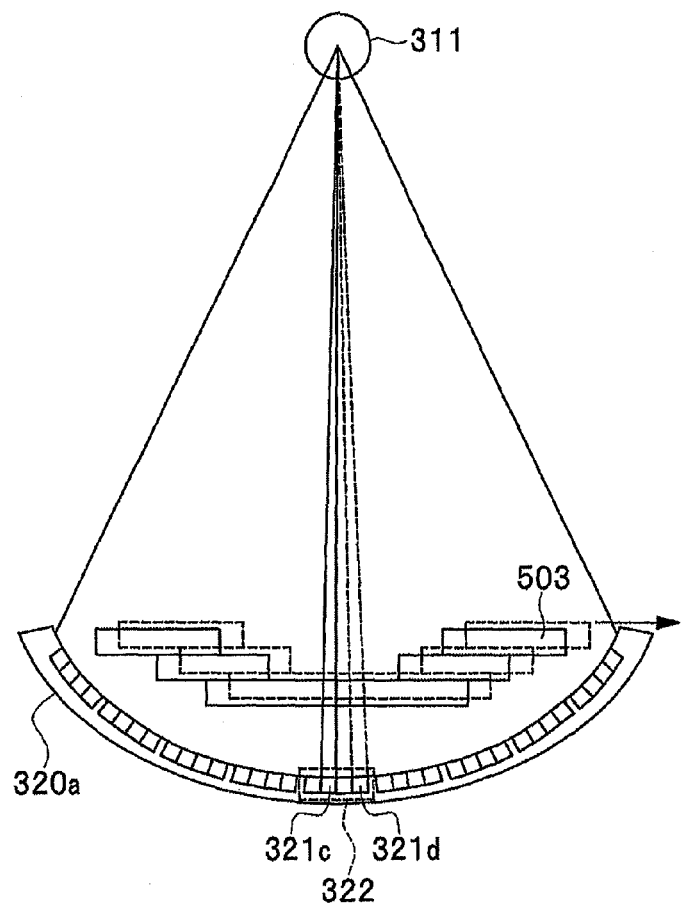
FIG. 5 is an illustration showing an X-ray detecting unit, related members and configuration, and a method of measuring a crosstalk quantity in a second embodiment, wherein (a) shows an illustration showing measurement of a signal with an X-ray detecting module in which some X-ray detecting units are combined, (b) is a chart showing a distribution of the signal quantity when light is applied to only an X-ray detector 321c, and (c) is a chart showing a distribution of a signal quantity when light is applied to only an X-ray detector d.
Figure 5:
Figure 5:

FIG. 5 is an illustration showing an X-ray detecting unit and related members and configuration and the method of measuring the crosstalk quantity in the second embodiment.

In FIG. 5, a fundamental structure and configuration is the same as that of the X-ray CT apparatus 100 shown in FIG. 1. However, there is a difference in a structure of the X-ray detecting unit 320 (see FIG. 1).

In the second embodiment shown in FIG. 5 (*a*), an X-ray detecting unit 320*a* is used. The X-ray detecting unit 320*a* is configured with a plurality of detecting modules 322 each including a plurality of the X-ray detectors 321 (321*c*, 321*d*, - - - ) combined.

In this case, the crosstalk of the X-ray detector 321 varies in characteristic, between, for example, the X-ray detector 321*c* at the middle of the detecting module 322 and an X-ray detector 321*d* at an edge part (see FIG. 5). FIG. 5 (*b*) is a chart showing a distribution of the signal quantity when light is applied to only the X-ray detector 321*c*, and FIG. 5 (*c*) is a chart showing a distribution of a signal quantity when light is applied to only the X-ray detector 321*d*.

However, it is frequent that a detecting module 322 including combined X-ray detectors 321 has substantially the same crosstalk characteristic as that of another detecting module.

Then, a difference between the edge part and the middle of the detecting module 322 is measured. As in the method of measurement in the first embodiment using a pinhole collimator designed to allow light to enter only one X-ray detector, the difference is measured between the signal originally incident to the X-ray detector 321 and s signal of light emitted from its circumference.

In this operation, only the detecting module 322 in FIG. 5 is measured and other modules are not measured. In other words, the detecting module 322 is dealt as a representative, and its characteristic is dealt as a common characteristic of the detecting modules, and measurement of other detecting modules are omitted.

A specific measurement method and a correction quantity calculation will be described with a flowchart of FIG. 6.

<Flowchart of Measurement Method and Correction Quantity Calculation>

Figure 6:
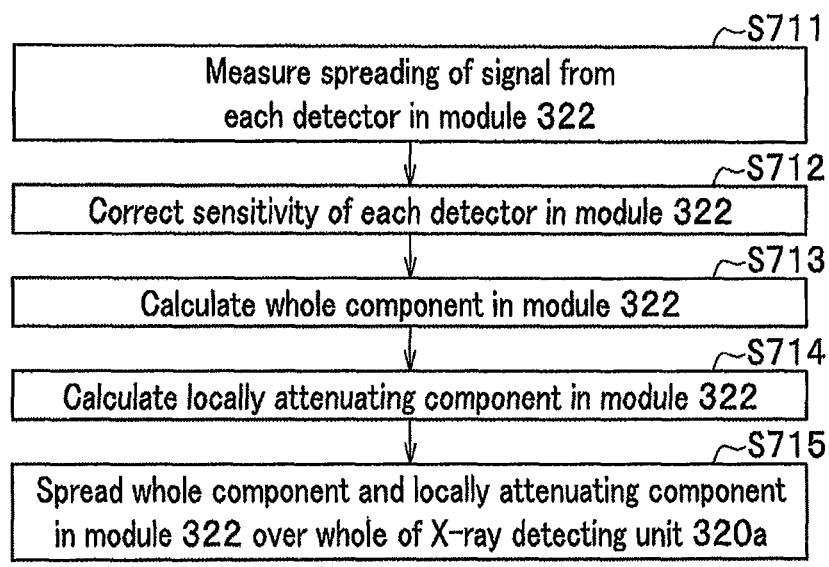
FIG. 6 is a flowchart showing a method of acquiring crosstalk correction data in the second embodiment of the present invention.

FIG. 6 is a flowchart showing a method of acquiring crosstalk correction data in the second embodiment of the present invention.

At first, the signal spreading from each of the detectors in the detecting module 322 is measured ("Measure spreading of signal from each detector in module 322" (step S711)).

As described in the first embodiment, using the shielding body 503 designed to allow light to enter only one X-ray detector, a signal originally to be incident and a signal of light emitted from its circumference (signal quantities when light is applied to only the X-ray detector 321c and the X-ray detector 321d (respectively shown in FIG. 5(b), FIG. 5 (c)) are measured. Next, from the acquired measured values, sensitivity-correction data is prepared similarly to the first embodiment.

Next, the sensitivity correction of the signal data acquired in the step S711 is performed as "Correct sensitivity of each detector in module 322" (step S712).

The method is similar to that in the first embodiment. However, performance of this may be omitted except the detecting module 322. This is based on assumption in that each of the modules is expected to have substantially the same characteristic as that of the detecting module 322.

Next, from the data after the acquired sensitivity correction the whole component relating to the crosstalk correction is calculated and extracted ("Calculate whole components in module 322") (step S713").

This is performed to only the X-ray detectors of the detecting module 322.

Next, the locally attenuating components are calculated ("Calculate local attenuating components in module 322") (step S714).

Also this is performed to only the X-ray detectors in the detecting module 322.

At last, the whole components and the locally attenuating components are spread out over the whole of the X-ray detecting unit 320a ("Spread whole components and local attenuating components in module 322 over whole of X-ray detecting unit 320a") (step S715).

More specifically, data of the whole components and the locally attenuating component is prepared in which that crosstalk correction quantities of the X-ray detector located at the same position relative to the detecting module 322 is presumed as the correction quantities measured in the detecting module 322.

This provides advantageous effects below in addition to the advantageous effects [1] and [2] described in the first embodiment.

[3] It is possible to shorten the correction measuring time by reducing the number of the detecting modules to be measured.

In addition to one detecting module, some (not the whole) of the detecting modules such as two or three detecting modules may be measured as a representative.

Further Advantageous Effect

In this case in addition to the advantageous effects [1] to [3], there are advantageous effects below.

[4] It becomes possible to suppress dispersion in correction measurement by averaging among a plurality of the X-ray detectors.

[5] When a part of the representative detecting module is failure, it is possible to detect the failure by comparison with another detecting module.

The correction is made using periodicity of the detecting module configuration. However, for example, also in another case where the difference in the local crosstalk occurs in association with the periodic configuration such as differences in the size of the X-ray detector, and thickness of a reflecting member inside the X-ray detector, the correction data can be prepared in accordance with the corresponding period.

Third Embodiment

In the second embodiment, a method of measuring locally attenuating quantities in the periodic configuration was described. In the third embodiment, a method of correction with the measurement with a phantom which is different from the shielding body in the second embodiment will be described.

The device configuration which is the same as that in the second embodiment shown in FIGS. 1 and 5 is used. A difference from the second embodiment is in that a phantom shown in FIG. 7 is used.

<Crosstalk Error Measuring Phantom>

Figure 7:
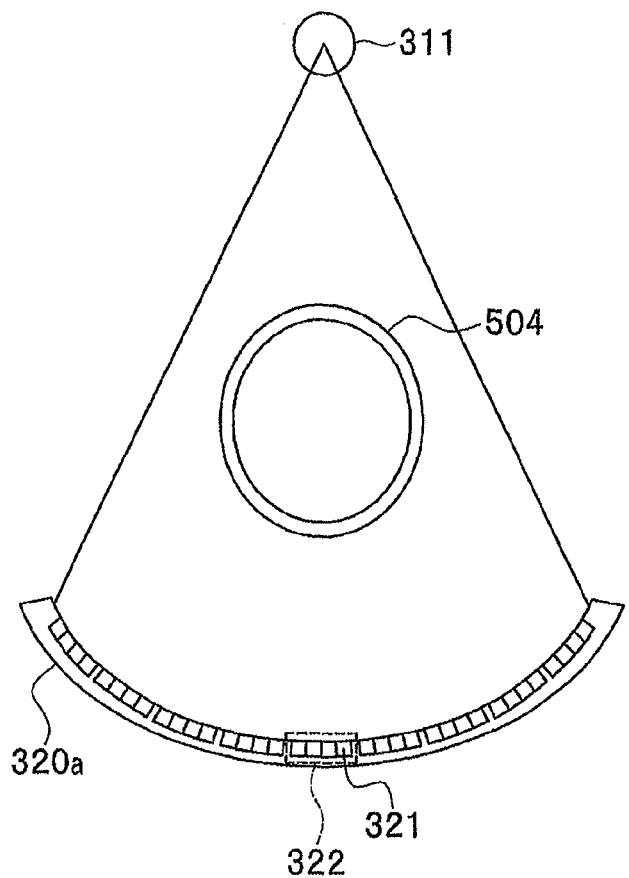
FIG. 7 is an illustration showing a method of measuring the crosstalk quantity in a third embodiment of the present invention, wherein (a) is an illustration of measuring the signal using a crosstalk error measuring method, and (b) is an illustration showing a status of artifact in a crosstalk error determining image in a measuring device shown in (a).
Figure 7:
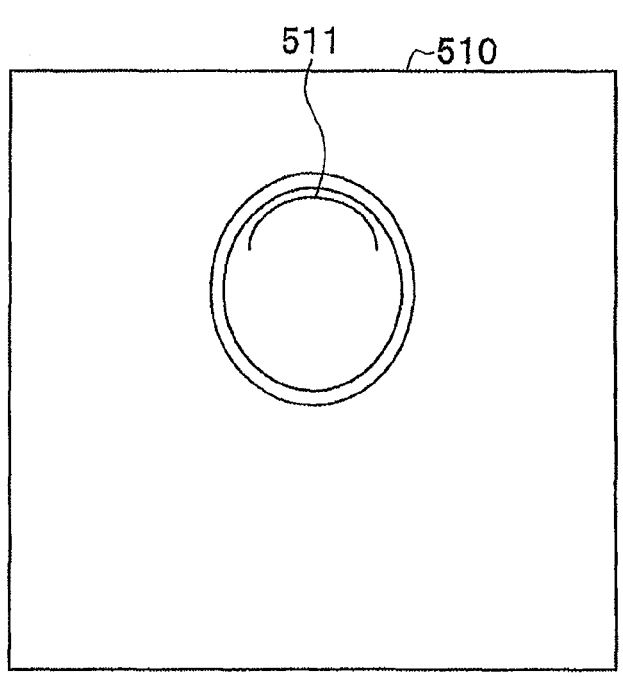

FIG. 7 is an illustration showing a method of measuring the crosstalk quantity in the third embodiment of the present invention.

As shown in FIG. 7 (a), a crosstalk error measuring phantom 504 is used instead the shielding body 503 (FIG. 5). As the crosstalk error measuring phantom 504, a phantom is used which has a large attenuation quantity and a large difference in the attenuation quantity, for example, Teflon (registered trademark) ring. At a part having a large difference in the attenuation quantity, there is a large difference between a quantity of entered and leaking quantity of crosstalk. This is because the leaking quantity of the crosstalk is in proportion to a signal quantity of light emitted.

Then using the phantom having a large difference in such an attenuation quantity, the measurement is made at a location where the difference in crosstalk is large. In this operation, the local attenuation correction quantity can be measured by checking whether the local attenuation correction is correctly performed. Regarding the sensitivity, it is previously corrected by another method.

FIG. 7 (b) shows a status in which an artifact 511 occurs in a crosstalk error determining image 510 in the measuring device shown in FIG. 7 (a).

<Measuring Method and a Flowchart of Correction>

Figure 8:
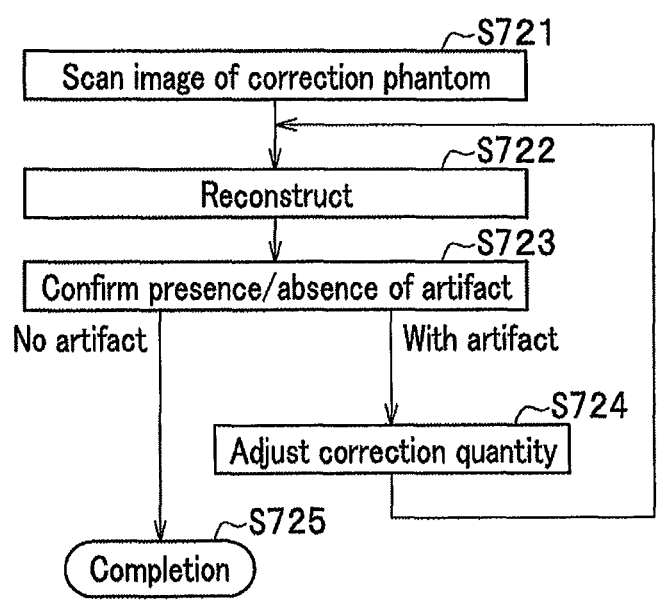
FIG. 8 is a flowchart showing a method of acquiring crosstalk correction data in the third embodiment of the present invention.

FIG. 8 is a flowchart showing a method of acquiring crosstalk correction data in the third embodiment of the present invention. With reference to the flowchart in FIG. 8 will be described a measuring method and correction. Here, occasionally FIG. 7 will be referred.

First, using the crosstalk error measuring phantom 504, "Scanning an image of a correcting phantom" is performed (step S721).

Next, data of the scanned image is reconstructed (step S722).

The reconstructed image is confirmed to "confirm whether the artifact is present or absent" (step S723).

As shown in FIG. 7, when the artifact 511 is generated as a ring or a streak at the location of the phantom (presence of the artifact), "adjust the correction quantity" is performed so as to cancel the artifact 511 (step S724).

To confirm whether the correction quantity is proper or improper, the data in the step S722 is returned to "reconstruct".

Because a polarity of a difference in a CT value of the artifact restructured from its circumference varies positive and negative between the cases of overcorrection and insufficient correction in correction quantity, the adjustment direction of the correction value can be grasped. This operation is repeated until the artifact 511 disappears.

In addition, a position of the phantom is changed, and when it can be confirmed that the artifact 511 is reduced at a plurality of locations, this provides a high effect in correction.

The measurement and adjustment of correction quantity is repeated, when the artifact disappears in the "confirmation whether the artifact is present and absent (absence of the artifact), measurement and the correction are completed (step S725).

In this method, it is possible to detect a deviation component regarding local variation and extract the correcting quantity. In other words, it is possible to acquire the local attenuation correction values. On the other hand, the optimal correction at each location is not always optimal correction in the whole image. Accordingly, it is difficult to acquire a correction value for the whole effect regarding optimal correction in the whole image only by the method of local correction.

<Correction to Whole Effect Using Resolution Measurement Phantom>

Then, regarding the correction to the whole effect, another phantom is used.

Regarding the correction of the whole components, instead of the crosstalk error measuring phantom 504, for example, a resolution measurement phantom is used.

The resolution measuring phantom has, for example, a configuration in which a plurality of slits are arranged with different intervals (gaps), and a resolution is measured according to how minimum length of the gap provides identification. Defining the correction to the whole component so as to make the resolution best maximizes the correction effect.

However, because depending on a part of a location an image quality may decrease due to increase in the noise component, the user is allowed not to set the resolution to the maximum correction effect, but can set the resolution to such a value that the user can find a difference between a disease variation and a normal part.

This method is allowed to be used only in case where a cause of generation of the artifact in the image can be determined as crosstalk. Though it is allowed that another artifact occurs, it is necessary to adjust parameters so as to reduce only the artifact caused by crosstalk by the process shown by the flowchart in FIG. 8.

Expected Advantageous Effect of Third Embodiment

According to the third embodiment, there are expected advantageous effects in addition to the advantageous effects [1] to [2] of the first embodiment.

[6] This can be carried out in a general scanning procedure, and it is not necessary to make such an adjustment that the X ray is applied to only one detector with the shielding body. As a result, the correction data acquiring operation becomes easy and a high speed processing is provided.

Other Embodiments

Only the third embodiment was described in which correction quantities of the whole component can be adjusted for every part of a target or every user. However, it is allowed that also in the first and second embodiments, it may be allowed to adjust the correction quantity of the whole component for every measurement value. In addition, when the correction quantity of the whole component is low, only the local components may be corrected without the correction to the whole component.

As described above, the X-ray CT apparatus according to the embodiments in performing the crosstalk correction, only correction of the locally attenuating component is performed previously, and correction of the whole component of the crosstalk is performed at the same time as the image reconstruction filter.

This provides an advantageous effect in operation reduction because only the locally attenuating components are operated, and advantageous effect of reduction in an operation cost and enhancement in an operation throughput because an operation quantity in reconstruction of the image is reduced due to reduction in the whole component operation.

DESCRIPTION OF REFERENCE CHARACTERS

100 X-ray CT apparatus
200 input unit
210 scanning condition input unit
21 keyboard
212 mouse
213 monitor
300 scanning unit
310 X-ray generating unit
311 X-ray tube
320, 320*a* X-ray detecting unit
321, 321*a*, 321*b*, 321*c*, 321*d* X-ray detector
322 detecting module
330 gantry
331 opening
332 rotating plate
340 scanning control unit
341 X-ray control unit
342 gantry control unit
343 table control unit
344 detector control unit
345 supervisory control unit
400 image generating unit
410 signal collecting unit
411 data acquisition system, DAS 420 data processing unit
421 central processing unit
422 memory
423 HDD device
440 image display unit
441 image display monitor
500 object body
501 object mounting table
503 shielding body
504 crosstalk error measuring phantom
510 crosstalk error determining image
511 artifact

The invention claimed is:

1. An X-ray CT apparatus, comprising:
an X-ray generating unit configured to generate X-rays;
an X-ray detecting unit including a plurality of X-ray detectors, each configured to detect the X-rays which are generated from the X-ray generating unit and transmitted through an object; and
an image generating unit configured to correct signals acquired by the X-ray detecting unit and reconstruct an image therefrom,
wherein the X-rays directed to a first of the X-ray detectors spread at the X-ray detecting unit as cross talk, and the image generating unit is configured to:
measure the X-rays directed to the first of the X-ray detectors with the first of the X-ray detectors and with a second and a third of the X-ray detectors which are positioned on both sides of the first of the X-ray detectors,
correct sensitivity differences of the signals acquired by the X-ray detectors in accordance with the signals detected by the first, second, and third of the X-ray detectors,
calculate a whole component of crosstalk correction from the sensitivity difference corrected signals, and
calculate a cross talk correction quantity for each of the X-ray detectors from the sensitivity difference corrected signals, and calculate a locally attenuating component for each of the X-ray detectors as a difference between a respective cross talk correction quantity and the whole component of crosstalk correction, and
wherein when crosstalk corrections of the plurality of the X-ray detectors are performed by the image generating unit, the image generating unit is configured to:
perform a crosstalk correction of each locally attenuating component using the whole component of crosstalk correction, and then reconstruct the image while correcting the signals from the X-ray detectors using a correction quantity of the whole component of crosstalk correction.

2. The X-ray CT apparatus as claimed in claim 1, wherein a shielding body causes the X-rays directed to a first of the X-ray detectors to spread at the X-ray detecting unit as cross talk.

3. The X-ray CT apparatus as claimed in claim 1,
wherein the plurality of the X-ray detectors are arranged periodically,
wherein the image is reconstructed while correcting the signals from the X-ray detectors using a correction quantity of the whole component of crosstalk correction to reduce an artifact present in the signals measured by the X-ray detecting unit.

4. An X-ray CT apparatus, comprising:
an X-ray generating unit configured to generate X-rays;
an X-ray detecting unit including a plurality of X-ray detectors, each configured to detect the X-rays which are generated from the X-ray generating unit and transmitted through an object; and
an image generating unit configured to correct signals acquired by the X-ray detecting unit and reconstruct an image therefrom,
wherein the X-rays directed to each of the X-ray detectors spreads to other X-ray detectors positioned on both sides thereof as crosstalk, and
wherein, for individual ones of the plurality of the X-ray detectors, the image generating unit is configured to:
measure the X-rays directed to a respective one of the X-ray detectors with the first of the X-ray detectors and with a pair of the X-ray detectors which are positioned next to the respective one of the X-ray detectors,
correct sensitivity differences of the signals detected by the respective one of the X-ray detectors and the pair of the X-ray detectors,
calculate a whole component of crosstalk correction from the sensitivity difference corrected signals, and
calculate a cross talk correction quantity for the respective one the X-ray detectors from the sensitivity difference corrected signals, and calculate a locally attenuating component for the respective one of the X-ray detectors as a difference between a respective cross talk correction quantity and the whole component of crosstalk correction, and
wherein when crosstalk corrections of the plurality of the X-ray detectors are performed by the image generating unit, the image generating unit is configured to:
perform a crosstalk correction of each locally attenuating component using the whole component of crosstalk correction, and then reconstruct the image while correcting the signals from the X-ray detectors using a correction quantity of the whole component of crosstalk correction.

5. The X-ray CT apparatus as claimed in claim 4, wherein the correction is performed using a distribution function of the crosstalk and values of the measured X-rays, for each of the plurality of detectors, for correcting a local crosstalk quantity of each of the plurality of the X-ray detectors.

6. The X-ray CT apparatus as claimed in claim 5, wherein the correction includes a Log conversion of the distribution function and the values of the measured X-rays, for each of the plurality of detectors, for correcting a local crosstalk quantity of each of the plurality of the X-ray detectors.

7. The X-ray CT apparatus as claimed in claim 4, wherein a shielding body is interposed between the X-ray generating unit and the X-ray detecting unit so that the X-rays directed to each of the X-ray detectors spreads to the other X-ray detectors as crosstalk.

8. The X-ray CT apparatus as claimed in claim 4,
wherein the plurality of the X-ray detectors are arranged periodically,
wherein a distribution function of the crosstalk and a plurality of correction values for correcting a local crosstalk quantity of the X-ray detectors are measured using less than all of the plurality of X-ray detectors, and
wherein the distribution of the crosstalk and the correction values for correcting the local crosstalk quantity of the remaining X-ray detectors and the average of crosstalk quantities for the remaining X-ray detectors are based on the measurements from less than all of the plurality of X-ray detectors.

9. The X-ray CT apparatus as claimed in claim 4,
wherein the plurality of the X-ray detectors are arranged periodically,
wherein the image is reconstructed while correcting the signals from the X-ray detectors using a correction quantity of the whole component of crosstalk correction to reduce an artifact present in the signals measured by the X-ray detecting unit.

\* \* \* \* \*